United States Patent [19]

Kubota

[11] 4,319,563
[45] Mar. 16, 1982

[54] ENDOSCOPE WITH A SMOOTHLY CURVED DISTAL END FACE

[75] Inventor: Tetsumaru Kubota, Hachioji, Japan

[73] Assignee: Olympus Optical Co., Ltd., Tokyo, Japan

[21] Appl. No.: 43,828

[22] Filed: May 30, 1979

[30] Foreign Application Priority Data

Dec. 2, 1977 [JP] Japan .................. 52-162018

[51] Int. Cl.³ .............................. A61B 1/06
[52] U.S. Cl. .............................. 128/6
[58] Field of Search .................. 128/3–9, 128/634; 350/96.26; 356/241

[56] References Cited

U.S. PATENT DOCUMENTS

| 3,132,646 | 5/1964 | Hett | 128/6 |
| 3,278,738 | 10/1966 | Clark | 128/6 |
| 3,426,663 | 2/1969 | Fox | 128/6 |
| 3,556,085 | 1/1971 | Takahashi | 128/6 |
| 3,655,259 | 4/1972 | Miyauchi et al. | 350/96.26 |
| 3,728,998 | 4/1973 | Heine | 128/9 |
| 3,796,214 | 3/1974 | Davis | 128/6 |
| 4,173,392 | 11/1979 | Ekinaka et al. | 350/96.26 |
| 4,204,528 | 5/1980 | Termanini | 128/6 |

FOREIGN PATENT DOCUMENTS

| 463992 | 3/1950 | Canada | 128/6 |
| 1269287 | 5/1968 | Fed. Rep. of Germany | 128/8 |
| 1961168 | 12/1969 | Fed. Rep. of Germany | 128/6 |
| 1054009 | 1/1967 | United Kingdom | 350/96.26 |

Primary Examiner—Robert W. Michell
Assistant Examiner—Daniel P. Burke

[57] ABSTRACT

One end portions of a plurality of light conducting optical fibers disposed inside an outer sheath of an endoscope which is to be inserted into a body cavity are exposed directly to the outside through an opened distal end of the sheath. The exposed end face is formed into a smooth, spherical convexity, for example.

3 Claims, 7 Drawing Figures

ENDOSCOPE WITH A SMOOTHLY CURVED DISTAL END FACE

BACKGROUND OF THE INVENTION

This invention relates to an improvement of the end face of an endoscope for observations of human body cavities and occasionally for medical treatment thereof, including an outer sheath to be inserted into the body cavities and a view window of an observation system disposed at the distal end of the sheath.

Generally, in this type it be endoscope, whether of a direct-viewing rigid type with an unbendable rigid sheath or of a flexible type with a flexible sheath, the distal end of the sheath is formed roundly and smoothly. This is done for the purpose of preventing the distal end portion of the sheath from damaging tissue inside a body cavity when the sheath is inserted into the body cavity.

In one such prior art endoscope, therefore, an annular distal end edge of the sheath is rounded to preclude the possibility of damage to the tissue. Such conventional consideration may not, however, provide a fully effective measure to counter such danger yet, since the outer sheath is generally a thin pipe or tube, so that the radius of curvature of rounding on the end edge, if any, is limited.

SUMMARY OF THE INVENTION

Accordingly, the object of this invention is to provide an endoscope including a sheath which has a rounded distal end face with improved smoothness and increased radius of curvature, thereby reducing the possibility of damage to living bodies and providing ease of manufacture as well as simpleness in construction.

In order to attain the above object, the endoscope of this invention is so constructed that distal-end-side end portions of a plurality of light conducting optical fibers, which are disposed longitudinally inside a sheath from the base or proximal end to the distal end thereof, are exposed directly to the outside through the opened distal end of the sheath to form a part of a distal end face of the sheath, and that the end face part formed of the fibers is smoothly curved into, for example, a spherical convexity.

Thus, a curved surface with a great radius of curvature is formed on the distal end face, so that the possibility of the end face's damaging the living bodies may be reduced. Further, since the exposed end portions of the optical fibers form part of the distal end face, there will not be required any means to cover the distal end face, such as a metallic cover or cap member, that would be essential to the prior art construction, leading to a reduction in manufacturing cost as well as easier assembling.

Moreover, the optical fibers exposed at the opened distal end of the sheath occupies the whole region of an end face portion except the regions of a view window and an opening or openings of a channel or channels for catheter insertion and/or water supply that are defined inside the sheath and open to the distal end.

Thus, a good quantity of light may be sent into a body cavity by means of the light conducting optical fibers.

Furthermore, one end portions of the optical fibers are hardened with an adhesive agent, and an end face of the hardened fibers exposed through the opened distal end of the sheath is finished together with an annular end edge of the sheath by grinding, thereby forming a smooth, continuous convex surface with an increased radius of curvature on the distal end face. Thus, the manufacture of the endoscope may highly be facilitated without requiring any special complicated process.

DETAILED DESCRIPTION OF THE PREFERRED EMBODIMENTS

Now there will be described preferred embodiments of this invention with reference to the accompanying drawings.

Figure 1:
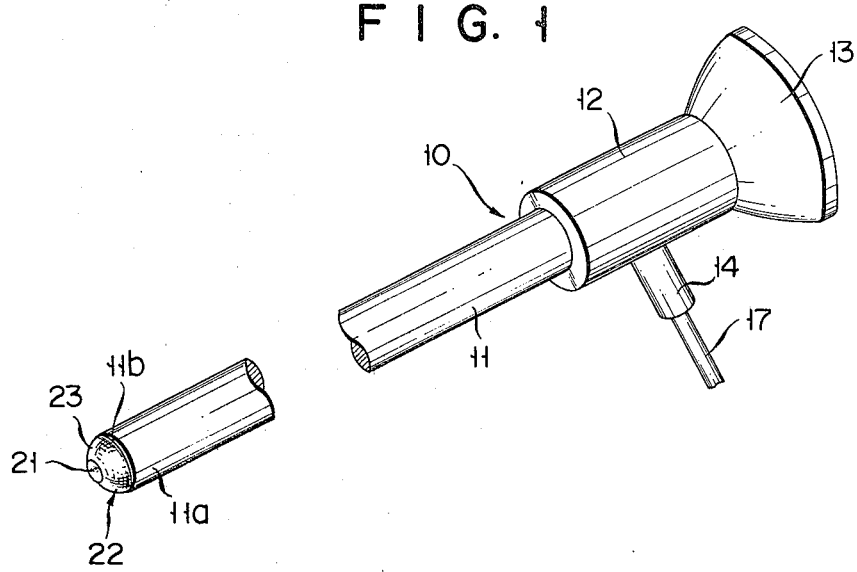
FIG. 1 is a perspective view of an endoscope with a smoothly curved end face at the distal end of a sheath according to an embodiment of this invention.

Referring now to the drawing of FIG. 1, an endoscope 10 is what is called a direct-viewing rigid scope with a rigid, elongated outer sheath 11. An eyepiece section 13 is attached to one end of a control section 12 at the proximal end portion of the sheath 11, while a light guide connector 14 is fixed to the side of the section 12.

Figure 2:
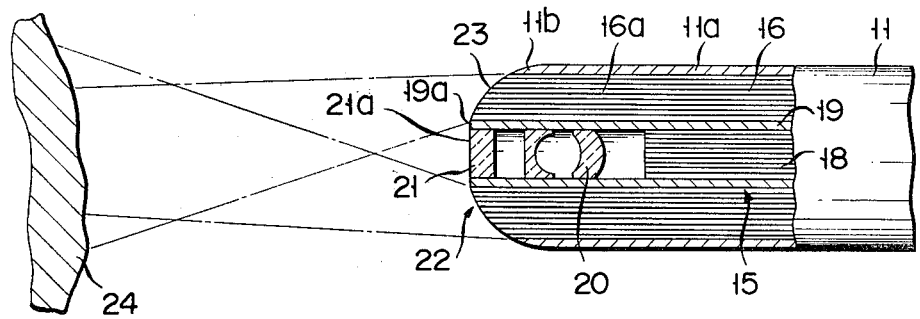
FIG. 2 is an enlarged partial profile of a distal end section of the endoscope as shown in FIG. 1.

Inside the cylindrical outer sheath 11, as partially shown in FIG. 2, an observation system 15 is disposed along the axis of the sheath 11, and a plurality of light conducting optical fibers 16 for illumination are compactly arranged round the observation system 15.

End portions (not shown) of the optical fibers 16 inside the control section 12 are connected to the light guide connector 14, and further connected to an external light source (not shown) by means of the connector 14 and a cord 17.

The observation system 15 extending along the axis of the sheath 11 includes an eyepiece (not shown) disposed at the eyepiece section 13 within the control section 12, an optical fiber bundle 18 with one end facing the eyepiece and the other end extending to a distal end 11a of the sheath 11, a tube 19 surrounding the fiber bundle 18, and a lens set 20 arranged opposite to the other end of the fiber bundle 18. Such construction, however, is generally known in the art, so that detailed description thereof will be omitted.

Said optical fiber bundle 18 of the observation system 15 may be replaced by a series of relay lens or an image transmitter with light-condensing function constituted by a plurality of cylindrical glass rod lenses.

At a portion of the observation system 15 which opens to the distal end 11a of the sheath 11, a cover glass member with a flat outer face 21a forming a view window 21 is fitted in one end portion of the tube 19. Thus, an observer may view the inside of a body cavity in which the sheath 11 is inserted, through the view window 21 as well as the observation system 15.

Figure 3:
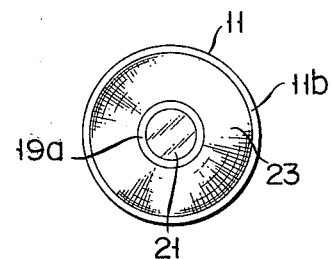
FIG. 3 is an end view of the section of FIG. 2.

Referring expressly to FIGS. 2 and 3, there will now be described the construction of the distal end of the sheath 11 which constitutes the point of this invention. At least end portions 16a on the distal end side of the light conducting optical fibers 16 that are closely tubularly arranged between the tube 19 of the observation system 15 and the outer sheath 11 are hardened as one body with a suitable adhesive agent. The hardened end portions 16a of the fibers are exposed directly to the outside through the opened distal end 11a of the sheath, forming a portion 23 of a distal end face 22 of the sheath. The end face portion 23 of the fibers, as well as an annular end edge 11b of the sheath 11, are ground into a smooth, continuous convexity spherical surface for this embodiment. The spherical end face portion 23 is connected with a flat end edge 19a of the tube 19 without a hitch. Accordingly, the whole of the end face 22 of the sheath including the outer glass face 21a of the view window and the end face portion 23 of the fibers forms quite a smooth face, providing no edge portion at the joint.

As may be seen from FIG. 2, the spherical part including the end face portion 23 of the fibers 16 and the end edge 11b of the sheath 11 have an extremely great radius of curvature. Further, as shown in FIG. 3, the view window 21, which is located just in the central-axis position of the end face 22, is concentrically annularly surrounded by the end face portion 23 of the fibers, and further the annular end edge 11b of the sheath is disposed around the outer periphery of the end face portion 23. Hereupon, it may be understood that the smooth end face portion 23 of the fibers occupies quite a large part of the end face 22.

Accordingly, there is provided, besides the smoothness of the end face 22, an advantage that a good quantity of light from the light source may be sent out into the body cavity through the wide end face portion 23 for illumination. Moreover, as shown in FIG. 2, the illumination light from the end face portion 23 is subject to a convex lens effect due to the convexity of the end face portion 23, so that it spreads out toward a body cavity 24. In addition, the pencils of illumination light overlap each other, as indicated by chain lines in FIG. 2. Therefore, sufficient illumination is applied also to a region inside the body cavity corresponding to the view window 21 on the extension of the central axis of the sheath 11, so that uneven illumination may be avoided.

Figure 7:
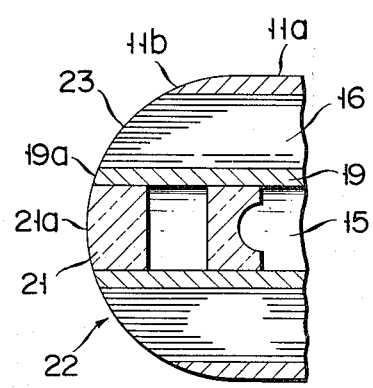
FIG. 7 is an enlarged partial profile of an endoscope according to still another embodiment of the invention showing a sheath with a perfectly spherical distal end face.

As shown in FIG. 7, the region of the view window 21 may also be curved so as to be in conformity with the curved surface of the end face portion 23 of the fibers.

In FIG. 7, like reference numerals refer to the same or corresponding parts as the ones shown in FIG. 2. An end face 22 of a sheath 11 of FIG. 7 forms a perfectly spherical convex surface along which an outer glass face 21a of a view window 21 and an end edge 19a of a tube 19 are curvedly formed. Naturally, if the outer face of the cover glass of the view window 21 is thus curved, the lens arrangement of an observation system 15 will be somewhat different. Such modification in design may be effected by one skilled in the art.

The aforementioned perfectly spherical end face 22 may be finished precise and smooth by grinding.

Figure 4:
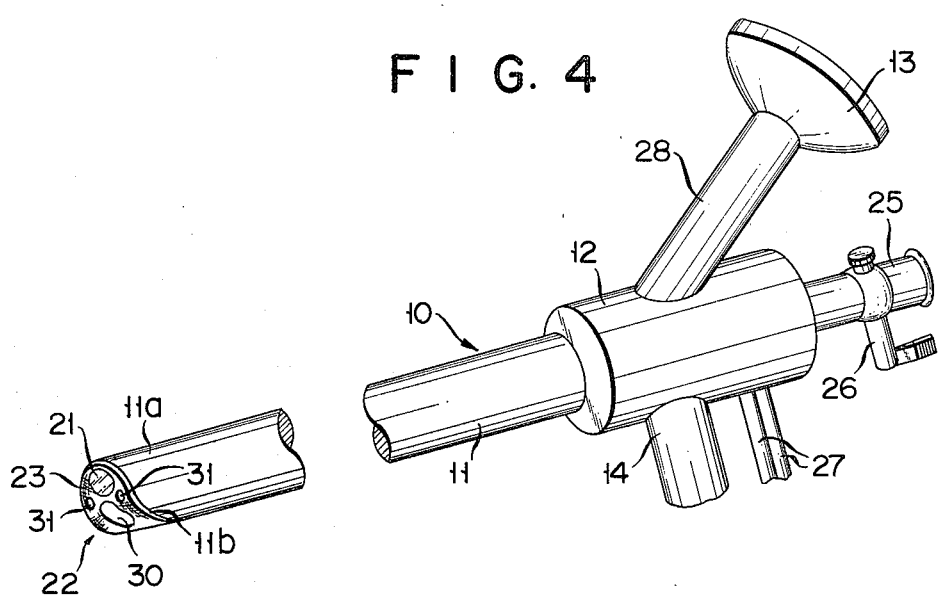
FIG. 4 is a perspective view of an endoscope according to another embodiment of the invention, further including channels for catheter insertion and water supply inside the sheath, in which the distal end face of the sheath is smoothly curved.
Figure 5:
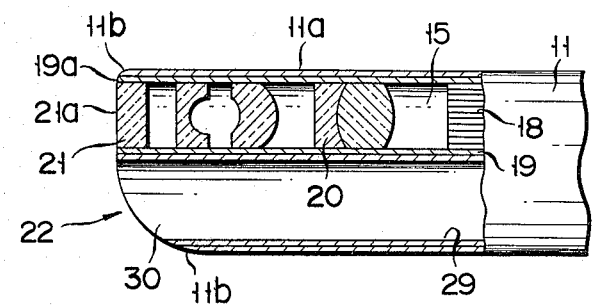
FIG. 5 is an enlarged partial profile of a distal end section of the endoscope as shown in FIG. 4.
Figure 6:
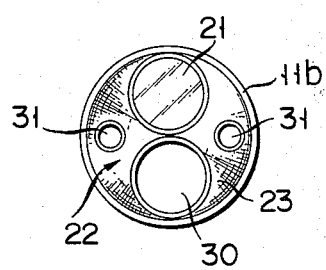
FIG. 6 is an end view of the section of FIG. 5.

An endoscope shown in FIGS. 4 to 6 is what is called a direct-viewing rigid scope as well, although it is additionally provided with a catheter insertion means and a water supply means. In these drawings, like reference numerals refer to the same or corresponding parts as the ones included in the first embodiment (FIGS. 1 to 3).

In FIG. 4, a control section 12 of the endoscope 10 is provided at an end with a catheter inlet 25 to which an inlet cock 26 is attached. Besides a light guide connector 14 and two pipe connector 27 for water supply, an observation system extension guide 28 protrudes aslant from the side of the control section 12, while an eyepiece section 13 is attached to the free end of the guide 28. Since such construction is generally known in the art, the connection with the internal arrangements will not be specifically described herein.

Inside an outer sheath 11, a channel 29 (FIG. 5) for catheter insertion and a pair of water supply channels (not shown) are arranged in parallel with an observation system 15 in the longitudinal direction of the sheath 11. One end of the catheter channel 29 opens into the catheter inlet 25, while the other end at a distal end 11a of the sheath has an opening 30. One end of each water supply channel communicates with each corresponding water supply pipe connector 27. At the respective other ends of the water supply channels on the distal end side of the sheath are openings 31 diametrically facing each other, as shown in FIG. 6.

At the distal end 11a of the sheath 11, the whole area of a portion 23 of an end face 22 except the regions of a view window 21 and the openings 30 and 31 of the channels is occupied by light conducting optical fibers, the portion 23 being smoothly convexed. Also, an annular end edge 11b of the sheath 11 is formed smoothly along the curved surface of the portion 23 so as to be in alignment therewith. As may be seen expressly from FIGS. 4 and 5, the end face portion 23 around the opening 30 of the catheter channel 29 is formed into a convexity with an extremely great radius of curvature.

Thus, also in this embodiment, the end portions of the optical fibers are exposed to the distal end of the sheath 11 over a wide area, so that the light conducting effect of the optical fibers may be good enough.

Moreover, in forming the end face 23, like the case of the first embodiment, the end portions of the optical fibers are first hardened with an adhesive agent, and then finished together with the end edge 11b of the sheath into a smooth convexity by grinding.

Furthermore, in this second embodiment, a flat surface remains in an outer face 21a of the view window 21 or cover glass member. As shown in FIG. 5, a portion of an end edge 19a of a tube 19 adjacent to the end edge 11b of the sheath is curved so as to conform with the end edge 11b, the remaining portion remaining flat.

As shown in FIG. 7, however, such flat portion may also be curved in alignment with the end face portion 23 of the optical fibers.

Although this invention has been described herein with rigid endoscopes given as the first and second illustrative embodiments thereof, it is to be understood that the invention may be also applicable to what is called flexible scopes with a flexible sheath.

What is claimed is:

1. An endoscope of the direct-viewing type comprising:
   a rigid elongated outer sheath having a distal end to be inserted into a body cavity, said distal end having a distal end face;
   an observation system longitudinally disposed inside said sheath for essentially the entire length of said sheath and having one end portion connected to a view window located in the distal end of said outer sheath, said view window having a smooth outer glass face disposed along the longitudinal centerline of said sheath in the center of the distal end face;

a plurality of light conducting optical fibers longitudinally arranged inside said outer sheath, said fibers having distal ends concentrically surrounding said view window, said fiber distal ends forming a portion of said distal end face and being ground to form an annular convexedly spherical distal end portion which forms a single continuous surface with said view window, said fiber distal ends being ground so that said annular convexedly spherical distal end portion is shaped to have a curvature which directs light from said fiber distal ends towards said view window so that light directed through some of said fibers overlaps light directed through others of said fibers to illuminate the region of the body cavity observed through said view window.

2. An endoscope according to claim 1, wherein an annular end edge of said sheath is formed smoothly to be in conformity with the annular end face portion of the optical fibers.

3. The endoscope of the direct-viewing type as defined in claim 1 wherein said outer glass face of the view window is curved to form a continuation of the curvature of said distal end portion.

* * * * *